(12) United States Patent
Lapidot et al.

(10) Patent No.: US 6,436,375 B1
(45) Date of Patent: Aug. 20, 2002

(54) METHOD FOR OBTAINING PHOTOSTABLE SUNSCREEN COMPOSITIONS

(75) Inventors: Noa Lapidot, Mevasseret Zion; Shlomo Magdassi, Jerusalem; David Avnir, Jerusalem; Claudio Rottman, Jerusalem; Orit Gans, M. P. Efraim; Alon Seri-Levy, Rehovot, all of (IL)

(73) Assignee: Sol-Gel Technologies Ltd., Tel Aviv (IL)

( * ) Notice: Subject to any disclaimer, the term of this patent is extended or adjusted under 35 U.S.C. 154(b) by 0 days.

(21) Appl. No.: 09/576,962

(22) Filed: May 24, 2000

Related U.S. Application Data

(60) Provisional application No. 60/136,030, filed on May 25, 1999.

(51) Int. Cl.⁷ .............. A61K 7/42; A61K 7/44; A61K 7/021; A61K 7/06; A61K 9/48
(52) U.S. Cl. .............. 424/59; 424/60; 424/63; 424/70.9; 424/400; 424/401; 424/451; 424/452; 424/490; 514/844; 514/944; 514/945; 514/972
(58) Field of Search .............. 424/400, 401, 424/59, 60, 451, 452, 490, 63, 70.9; 514/844, 944, 945, 972

(56) References Cited

U.S. PATENT DOCUMENTS

| | | | | |
|---|---|---|---|---|
| 4,129,645 A | * | 12/1978 | Barnett et al. | 424/60 |
| 5,387,622 A | * | 2/1995 | Yamamoto | 523/102 |
| 5,556,617 A | * | 9/1996 | Ribier et al. | 424/78.02 |
| 5,585,090 A | * | 12/1996 | Yoshioka et al. | 424/59 |
| 5,733,531 A | * | 3/1998 | Mitchnick et al. | 424/59 |
| 5,876,699 A | * | 3/1999 | DiSomma et al. | 424/59 |
| 6,090,399 A | * | 7/2000 | Ghosh et al. | 424/409 |
| 6,217,852 B1 | * | 4/2001 | Gildenberg et al. | 424/59 |

* cited by examiner

Primary Examiner—Jose' G. Dees
Assistant Examiner—Marina Lamm
(74) Attorney, Agent, or Firm—Lowe Hauptman Gilman & Berner, LLP

(57) ABSTRACT

The present invention relates to a method for obtaining improved photostability of a sunscreen composition that contains at least two sunscreen active ingredients, which are photo-unstable when formulated together, by microencapsulating at least one of said active ingredients in an encapsulating material suitable for holding the encapsulated active ingredient material, thus reducing or preventing its leaching out of the capsules; and adding other acceptable components and additives needed for the preparation of said composition. The sunscreen active ingredients can be selected from UVA and UVB absorbers, preferably a combination thereof. In a preferred embodiment of the present invention said active ingredients are encapsulated in separate sol-gel microcapsules.

20 Claims, 8 Drawing Sheets

METHOD FOR OBTAINING PHOTOSTABLE SUNSCREEN COMPOSITIONS

RELATED APPLICATIONS

The present application claims priority of U.S. Provisional Application Ser. No. 60/136,030, filed May 25, 1999, entitled "A METHOD OBTAINING PHOTOSTABLE SUNSCREEN COMPOSITIONS", the disclosure of which is incorporated by reference herein in its entirety.

FIELD OF THE INVENTION

The present invention relates to a method for obtaining sunscreen compositions with improved photostability in both the UVA and UVB regions, said method improves photostability by the encapsulation of sunscreen active ingredients (which are photodegraded when present together in the same sunscreen composition) in separate microcapsules and by incorporating said microcapsules into any acceptable vehicle.

BACKGROUND OF THE INVENTION

With the growing demand for higher SPF values and for broad-spectrum protection, manufacturers are forced to combine several active ingredients hence the problem of photo-induced cross reactivity between sunscreen active ingredients is becoming more severe.

For example, butyl methoxydibenzoylmethane (other known names: 4-tert-butyl-4'-methoxydibenzoylmethane, Avobenzone, BMDBM) was recently listed as category 1 in FDA's Final Monograph for OTC Sunscreen Products. However, this excellent UVA absorber presents a number of formulation problems. (W. Johncock, Sun Protection The Influencing Factors in Creating Effective Products, March 1999 London, March 1999 and references therein). A major problem of this sunscreen compound is the photoinduced interaction with the most widely used UVB absorber octylmethoxycinnamate (R. M. Sayre et. al, $26^{th}$ Annual Meeting if the American Society for Photobiology, Abstr. No. SPM-A7). This cross reactivity contributes significantly to the photochemical instability of both the UVB and the UVA active ingredients. The photostability issue when combining UVA with UVB filters seems to be more general than the case of BMDBM and OMC. In the same paper by Johncock, he reveals that new UVA chromophors examined as candidates for new products have been discarded as they were found to interact with OMC in an unacceptable way.

Photoinduced interactions of BMDBM restrict also the incorporation of this absorber with physical sunscreen agent such as titanium dioxide. In the US, formulation of BMDBM together with $TiO_2$ or ZnO is not allowed.

Several patents, for example WO94/04131 and EP780119, have been published regarding the improved photostability of BMDBM in the presence of other sunscreen ingredients such as Octocrylene, p-methyl-benzylidene camphor and others, at certain molar ratios. These patents, however, do not mention cinnamic acid derivatives and in particularly do not mention OMC, which is currently the most widely used UVB absorber. In practice, many popular products of broadband light screening compositions contain OMC and BMDBM as the main UV absorbers. Unfortunately, the photostability of many such products is poor, and stabilization by Octocrylene or p-methyl-benzylidene camphor is insufficient.

Patents EP 0 920 858 A2 and U.S. Pat. No. 5,985,251 teach that improved photostability of compositions based on benzylidene derivatives and cinnamic acid derivatives may be obtained by using a water soluble cinnamic acid derivative along with a fat soluble benzylidene derivative. Assuming that photo-instability results from a diffusion controlled reaction between exited species of the sunscreen agents, it may be rationalized that the separation of the two incompatible actives into different phases enhances stability by creating a diffusional barrier.

The method disclosed here teaches that improved photostability is achieved by creating an efficient diffusional barrier through effective encapsulation of at least one of two incompatible sunscreen actives, as in the case of cinnamic derivatives and dibenzoylmethane derivatives. In a preferred embodiment of this invention, both incompatible sunscreen actives are encapsulated separately.

The method presented in this invention is not limited to any specific combination of UVB and UVA absorbing ingredients, and affords further improvement in the photostability over prior stabilization methods.

According to the method of the present invention there is no formulation restriction concerning the ratio between UVA and UVB absorbers, thus any desired UVA/UVB protection ratio can be achieved.

SUMMARY OF THE INVENTION

The present invention provides a method for obtaining improved photostability of a sunscreen composition that contains at least two sunscreen active ingredients, which are photo-unstable when formulated together, comprising (a) microencapsulating at least one of said active ingredients in an encapsulating material suitable for holding the encapsulated active ingredient material, thus reducing or preventing its leaching out of the capsules; and (b) adding other acceptable components and additives needed for the preparation of said composition.

According to the invention the sunscreen active ingredients are selected from the group consisting of UVA absorbers and UVB absorbers, preferably encapsulated in sol-gel microcapsules.

In one embodiment the improved photostability of a sunscreen composition can be obtained by encapsulating each of the active ingredients in separate sol-gel microcapsules.

In another embodiment at least one of the sunscreen active ingredient is not encapsulated.

According to the present invention one of the sunscreen active ingredients can be a dibenzoylmethane derivative, preferably selected from a group consisting of 4-tert-butyl-4'-methoxydibenzoylmethane, 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane and 2,6-dimethyl-4-tert-butyl-4'-methoxy-dibenzoylmethane.

According to one preferred embodiment the sunscreen active ingredients are 4-tert-butyl-4'-methoxydibenzoylmethane and 2-ethylhexyl 4-methoxycinnamate.

According to another preferred embodiment the sunscreen active ingredients are 2-ethylhexyl p-methoxycinnamate and cinoxate.

The 4-tert-butyl-4'-methoxydibenzoylmethane can be co-encapsulated with homosalate, with 2-cyano-3,3- diphenylacrylic acid 2-ethylhexyl ester, or with a suitable cosmetic oil such as dicaprylyl maleate, Capric triglyceride, caprylic triglyceride, octyl palmitate, C12–C15 alkyl benzoate, dioctyl maleate, dioctyl malate, propylene glycol dicaprylate, propylene glycol dicaprate, diisopropyl adipate, hexyl laurate, and mixtures thereof.

The composition of the present invention can further include a physical sunblock active ingredient selected from the group consisting of titanium dioxide, zinc oxide, iron oxide, and mixtures thereof, wherein the physical sunblock ingredient can be of any commercially available grade, including surface treated particles such as titanium dioxide particles which have been surface treated with silica, alumina, stearic acid or by any other surface treatment.

The sunscreen composition of the present invention can be incorporated into a cosmetically acceptable formulation for use for the protection of human epidermis or hair against UV radiation.

The sunscreen compositions can be in the form of a lotion, a cream, a milk, a gel, an oil, an aerosol, a spray, a foam, a solid stick, a powder, a shampoo, a hair conditioner, a lacquer or a make up.

BRIEF DESCRIPTION OF THE FIGURES

FIG. 7.B- transmittance spectra of a composition containing sol-gel encapsulated OMC and sol-gel encapsulated BMDBM+Octocrylene in separate microcapsules (same concentrations as in FIG. 7.A) at increasing MED doses.

DETAILED DESCRIPTION OF THE INVENTION

Figure 1:
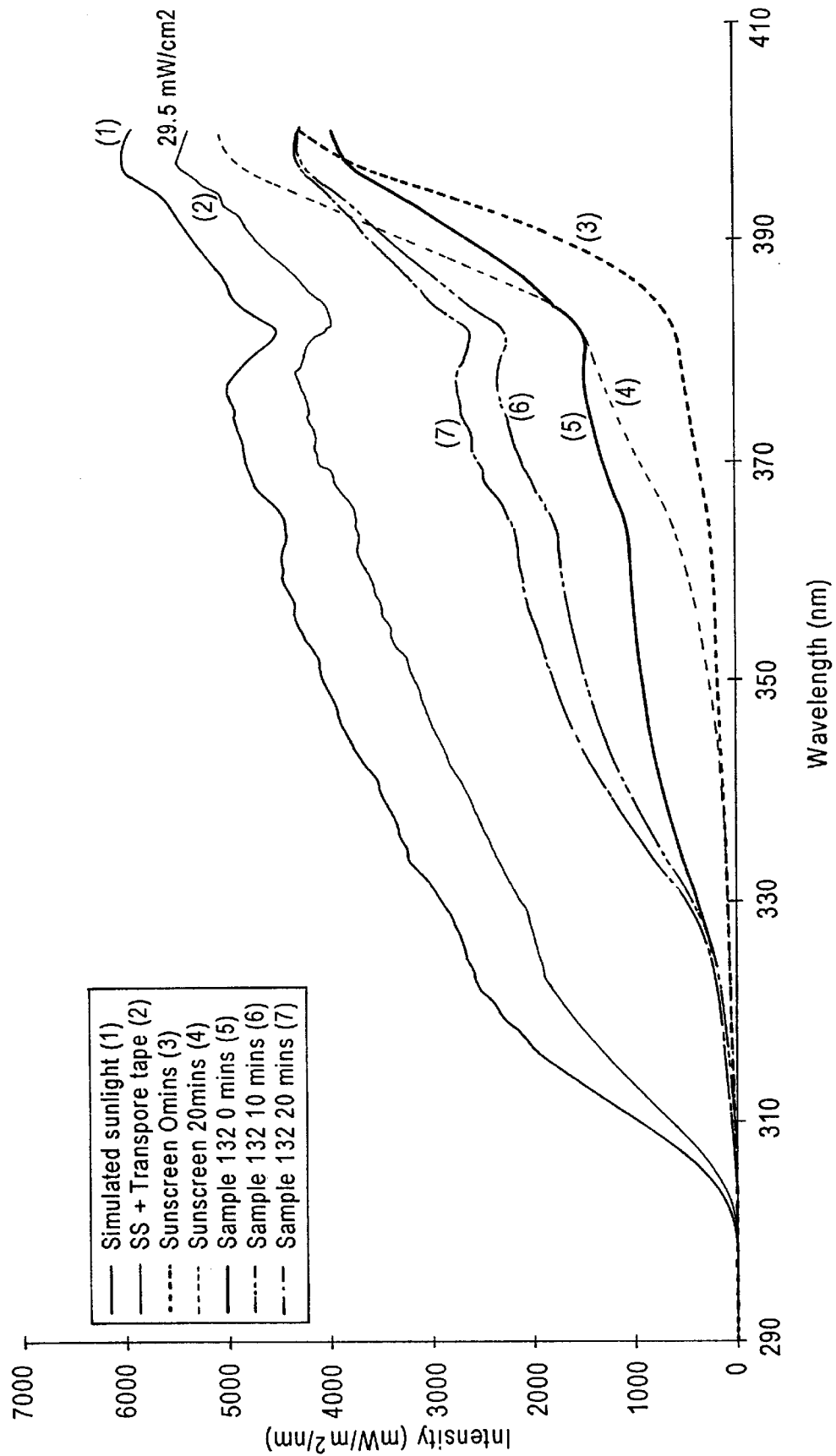
FIG. 1: transmittance spectra of sample 132 (containing co-encapsulated OMC and BMDBM) during illumination: simulated sunlight spectrum (line 1); simulated light through Transpore® tape (line 2); commercial sunscreen product at 0 min. illumination (line 3); commercial sunscreen product at 20 min. illumination (line 4); sample 132 at 0 min (line 5); 10 min. (line 6) and 20 min. illumination (line 7).
Figure 2:
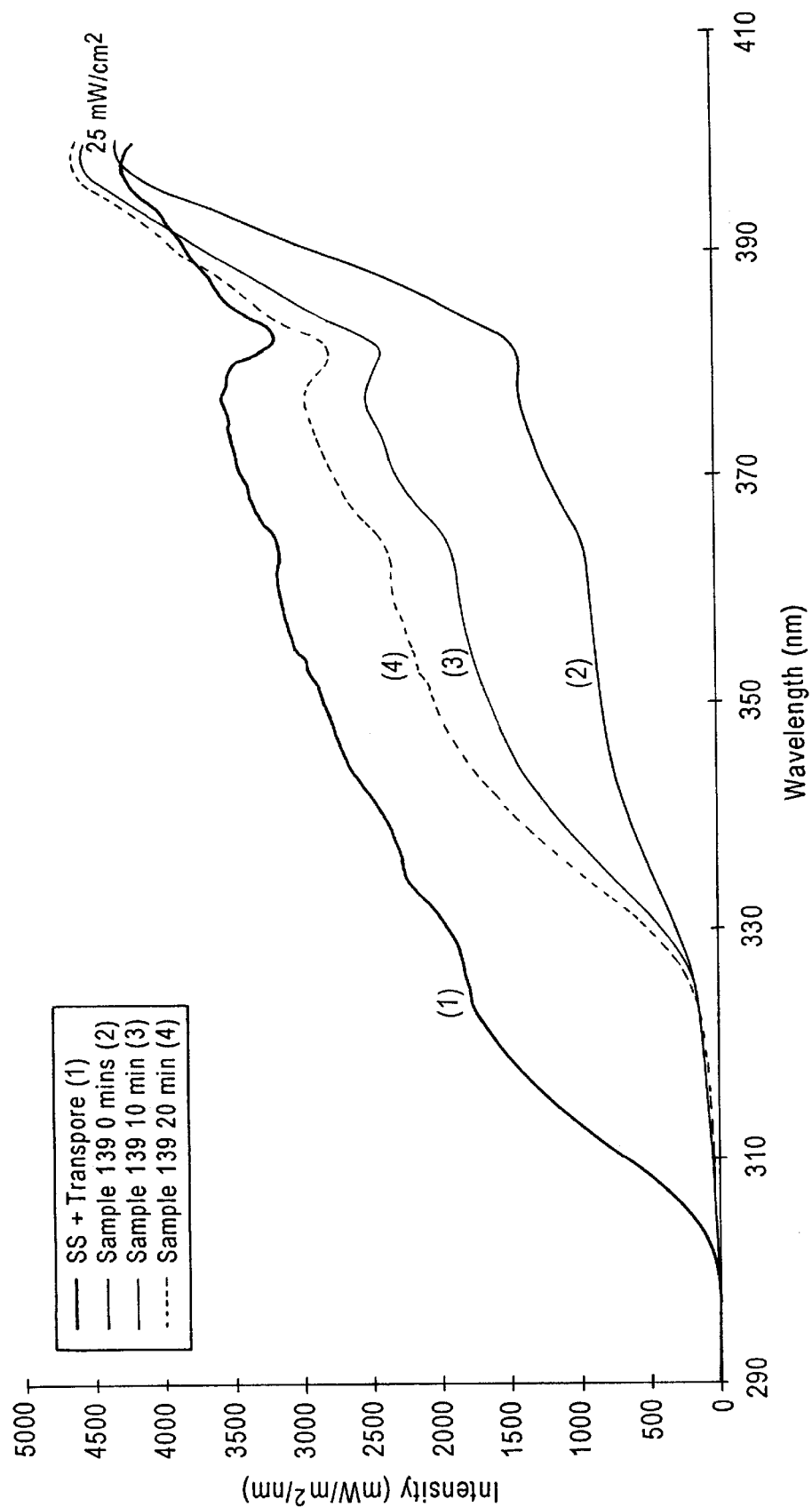
FIG. 2: transmittance spectra of sample 139 (containing free OMC and BMDBM) during illumination: simulated light through Transpore® tape (line 1); sample 139 at 0 min (line 2), 10 min (line 3) and 20 min illumination (line 4).

The method presented in this invention allows the co-formulation of at least two sunscreen ingredients (which are photodegraded when present together in the same sunscreen composition) while maintaining high photostability of reagents. This is done through their separate encapsulation, which reduces or even prevents the destructive reactions between them or their illumination products. In another embodiment of the present invention this is done by encapsulating only one or some of the active ingredients while the other active ingredient/s are present in the composition in a non-encapsulated form.

Effective encapsulation, that holds the sunscreen active ingredients within the capsules and reduces or even prevents their leaching out, creates a barrier that reduces or even prevents cross reactivity. Consequently, photostable formulations are obtained. In another embodiment of this invention, photostability is achieved through the encapsulation of one or more sunscreen ingredient in capsules that reduce or even prevent the leaching out of the encapsulated material, and the diffusion into the capsules of other sunscreen active ingredients that are present in the formulation in a non-encapsulated form.

A special case of the invention relates to sunscreen compositions where sol-gel derived capsules are used to create such barrier.

This stabilization method is particularly efficient for stabilizing sunscreen formulations that contain octyl methoxycinammate (OMC, 2-ethylhexyl-4-methoxycinnamate) or Padimate-O (both UVB absorbers) and 4-tert-butyl-4'-methoxydibenzoylmethane (a UVA absorber), with or without additional UVB absorbers such as 3,3,5-trimethyl-cyclohexyl-salicylate (Homosalate) or 2-cyano-3,3-diphenylacrylic acid 2-ethylhexyl ester (Octocrylene), or in the presence of cosmetic oils which may be co-encapsulated with 4-tert-butyl-4'-methoxydibenzoylmethane. Several sunscreen active ingredients may be co-encapsulated, providing they do not cause photodegradation when in contact with each other.

The method revealed in the present invention to enhance photostability through separate encapsulation of incompatible ingredients is general and can be applied to any known sunscreen active ingredients as well as to those still to be found.

The method is not limited to the preparation of sunscreen compositions for human application but can be applied to any sunscreen composition that is used for the protection against the sun radiation for any object that is exposed to such a radiation.

The benefits derived from this invention can be obtained via the use of various effective encapsulation technologies and encapsulation materials. Suitable microencapsulation can be obtained via a solvent evaporation method, a coacervation method, or an interfacial polymerization method. Such encapsulation technologies are familiar to the person skilled in the art.

In the solvent evaporation method, the sunscreen active ingredient is dissolved in a volatile solvent, which is insoluble in water. In the same solution, a polymer such as polylactic acid is dissolved. Thereafter, the solution is added to an aqueous solution, which contains an emulsifier such as ethoxylated sorbitan monolaureate (Tween 20, ICI). After high shear mixing, an emulsion is formed. The solvent is removed by evaporation under reduced pressure, resulting in the formation of microspheres, which contain the sunscreen agent entrapped within the polymer matrix.

In the coacervation method, the sunscreen is dissolved in a non volatile solvent (i.e. soybean oil), or used as is if liquid, and emulsified in water which contain gelatin. After an emulsion with proper particle size is formed, a coacervation agent, such as $Na_2SO_4$ is added, leading to coacervation of the gelatin around each droplet. Thereafter, a cross linking agent such as gluteraldehyde is added thus forming a rigid wall around the oil droplets.

In the interfacial polymerization method, a suitable monomer is dissolved in the sunscreen agent (when liquid), or in a solution containing the sunscreen active ingredient, and then emulsified in an aqueous solution which contains a suitable emulsifier. After the emulsion is formed, a second monomer, which is water soluble, is added to the emulsion. The polymerization occurs at the oil-water interface of the droplets, resulting in the formation of a wall. The monomers can be chosen so as to promote a variety of interfacial polymerization products as wall material; e.g. polyamides, polyesters, polyureas.

In the preferred embodiment of this invention the encapsulation method uses a sol-gel method, most preferably sol-gel silica. In this method, microcapsules of sunscreen active ingredients can be prepared by sol-gel method as revealed in U.S. application Ser. No. 09/372,176: the sunscreen active ingredient is dissolved in the sol-gel precursors wherein the sol-gel precursors can be a metal or a semi-metal alkoxide monomer, or a partially hydrolyzed and partially condensed polymer thereof, or a mixture of any of the above. This solution is emulsified under high shear forces in an aqueous solution, containing surfactants that assist in stabilizing the emulsions, such as cetyltrimethylammonium chloride. The obtained emulsion is mixed with an aqueous solution at a suitably selected pH (basic, neutral or acidic), until spheres containing the encapsulated sunscreen agent are formed.

Particularly, this invention may be applied to achieve photostable broadband sunscreen compositions consisting of dibenzoylmethane derivatives as the UVA absorber in the presence of UVB absorbers such as OMC, in the same formulation. These dibenzoylmethane may be selected out of the group consisting of 4-tert-butyl-4'-methoxydibenzoylmethane, 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane and 2,6-dimethyl-4-tert-butyl-4'-methoxy-dibenzoylmethane.

In a preferred embodiment of this invention, sol-gel capsules containing BMDBM and homosalate in one part are co-formulated with sol-gel capsules containing OMC in a cosmetic composition. The resulting formulation is photostable, whereas a similar formulation containing the same ingredients at the same concentration is unstable photochemically.

In another preferred embodiment, sol-gel capsules containing BMDBM and Octocrylene in one part are co-formulated with sol-gel capsules containing OMC in a cosmetic composition. The resulting formulation is photostable, whereas a similar formulation containing the same ingredients at the same concentration is significantly less photostable.

In yet another preferred embodiment, sol-gel capsules containing BMDBM in dicaprylyl maleate in one part are co-formulated with sol-gel capsules containing OMC in a cosmetic composition. The resulting formulation is photostable, whereas a similar formulation containing the same ingredients at the same concentration is significantly less photostable.

In yet another preferred embodiment, sol-gel capsules containing OMC are co-formulated with non-encapsulated BMDBM, in a cosmetic composition which is an emulsion, where BMDBM is dissolved in the organic phase of said emulsion. The resulting formulation is photostable, whereas a similar formulation containing the same ingredients at the same concentration is significantly less photostable.

In yet another preferred embodiment, sol-gel capsules containing BMDBM are combined in a cosmetic composition with inorganic sunscreen active ingredients such as titanium dioxide, zink oxide or iron oxides.

EXAMPLES

The following examples clarify and demonstrate the invention and are not under any circumstances exclusive.

Example 1

Preparation of Microcapsules for Sunscreen Active Ingredients Separation by a Sol-gel Method Microcapsules of sunscreen active ingredients can be prepared by sol-gel method as revealed in U.S. application Ser. No. 09/372,176: the sunscreen active ingredient is dissolved in the sol-gel precursors wherein the sol-gel precursors can be a metal or a semi-metal alkoxide monomer, or a partially hydrolyzed and partially condensed polymer thereof, or a mixture of any of the above. This solution is emulsified under high shear forces in an aqueous solution, containing surfactants that assist in stabilizing the emulsions, such as cetyltrimethylammonium chloride. The obtained emulsion is mixed with an aqueous solution at a suitably selected pH (basic, neutral or acidic), until silica spheres containing the encapsulated sunscreen agent are formed. Appropriate choice of the reaction condition facilitates the formation of spheres of the desired particle size, that hold the encapsulated sunscreen ingredients very efficiently, resulting in very low leaching rates of the encapsulated.

The resulting suspension of silica spheres containing encapsulated sunscreen active is incorporated into sunscreen compositions as shown in the following examples.

The separate encapsulation of sunscreen active ingredients, to achieve separation of ingredients that induce photodegradation when combined, results in improved photostability of the formulation, as demonstrated in example 9 and 10.

Example 2

Oil in Water Sunscreen Composition Containing Encapsulated Sunscreen Actives

|   | INCI name | % w/w |
|---|---|---|
| PHASE A | | |
| 1 | Squalane | 5.00 |
| 2 | Cetyl alcohol | 2.50 |
| 3 | Glyceryl stearate & PEG-100 stearate | 5.00 |
| 4 | Propylparabene | 0.10 |
| PHASE B | | |
| 5 | Aqua (water) | 36.6 to 66.6 |
| 6 | Methylparabene | 0.20 |
| 7 | Disodium EDTA | 0.05 |
| 8 | Imidazolidinyl urea | 0.50 |

-continued

| | INCI name | % w/w |
|---|---|---|
| PHASE C | | |
| 9 | Methylchloroisothiazolinone & Methylchlorothiazolinone & Benzyl alcohol | 0.05 |
| PHASE D | | |
| 10 | Silica suspension containing the sunscreen active to the desired concentration | 20 to 50 |

Phase A was heated to 75° C. and mixed. Phase B was heated to 75° C. and mixed. Phase B was poured into phase A and stirred for 5 minutes, followed by 25 minutes homogenization. The mixture was cooled to 55° C., and phase C was added while stirring. The mixture was cooled further to 40° C. and phase D was added while stirring. The cream was stirred for another 5 minutes.

Example 3
Comparative Example Oil in Water Sunscreen Composition Containing Free OMC The composition was prepared according to example 2, except that OMC was dissolved in phase A to afford 7.5% in the final composition, and the silica suspension was replaced with water.

Example 4
Oil in Water Sunscreen Composition Containing Encapsulated Sunscreen Actives

| | INCI name | % w/w |
|---|---|---|
| PHASE A | | |
| 1 | Brij 700 | 0.75 |
| 2 | Behenyl alcohol | 1.50 |
| 3 | Glyceryl stearate | 1.20 |
| 4 | Cyclomethicone | 2.00 |
| PHASE B | | |
| 5 | Aqua (water) | 65.85 |
| 6 | Glycerin | 2.70 |
| 7 | Disodium EDTA | 0.20 |
| 8 | Pectin | 0.30 |
| PHASE C | | |
| 9 | Silica suspension containing 35% OMC | 25.00 |
| PHASE D | | |
| 10 | Phenonip | 0.50 |

Phases A and phase B were heated separately to 80° C. Phase A was added to phase B and homogenized for 1 minute. The mixture was cooled to 40–50° C. with stirring. Phase C was added and homogenized for 1 minute. The mixture was cooled to r.t. and phase D was added with stirring. The pH was adjusted to 5.0.

Example 5
Oil in Water Sunscreen Composition Containing Encapsulated Sunscreen Actives and TiO$_2$

| | INCI name | % w/w |
|---|---|---|
| PHASE A | | |
| 1 | Brij 700 | 0.75 |
| 2 | Behenyl alcohol | 1.50 |
| 3 | Glycerylstearate | 1.20 |
| 4 | Cyclomethicone | 2.00 |
| 5 | C12–15 Alkyl benzoate, Titanium dioxide triethyl citrate, Alumina, Dimethicone Polyglycerin-3-diisostearate | 5.0 |
| PHASE B | | |
| 6 | Aqua (water) | 60.85 |
| 7 | Glycerin | 2.70 |
| 8 | Disodium EDTA | 0.20 |
| 9 | Pectin | 0.30 |
| PHASE C | | |
| 10 | Silica suspension containing 35% OMC | 25.00 |
| PHASE D | | |
| 11 | Phenonip | 0.50 |

Phases A and phase B were heated separately to 80° C. Phase A was added to phase B and homogenized for 1 minute. The mixture was cooled to 40–50° C. with stirring. Phase C was added and homogenized for 1 minute. The mixture was cooled to r.t. and phase D was added with stirring. The pH was adjusted to 5.0.

Example 6
Comparative Example of Oil in Water Sunscreen Composition Containing Free OMC

| | INCI name | % w/w |
|---|---|---|
| PHASE A | | |
| 1 | Brij 700 | 0.75 |
| 2 | Behenyl alcohol | 1.50 |
| 3 | Glyceryl stearate | 1.20 |
| 4 | Cyclomethicone | 2.00 |
| 5 | OMC | 8.80 |
| PHASE B | | |
| 6 | Aqua (water) | 82.05 |
| 7 | Glycerin | 2.70 |
| 8 | Disodium EDTA | 0.20 |
| 9 | Pectin | 0.30 |
| PHASE C | | |
| 10 | Phenonip | 0.50 |

Phases A and phase B were heated separately to 80° C. Phase A was added to phase B and homogenized for 1 minute. The mixture was cooled to r.t with stirring. Phase D was added with stirring and the pH was adjusted to 5.0.

Example 7
Oil in Water Sunscreen Composition Containing Encapsulated Sunscreen Actives

| | INCI name | % w/w |
|---|---|---|
| PHASE A | | |
| 1 | cetyl dimethicone copolyol | 3.00 |
| 2 | Isohexadecane | 9.50 |

-continued

|   | INCI name | % w/w |
|---|---|---|
| 3 | Cetearyl isonanoate | 7.75 |
| 4 | Octyl stearate | 7.75 |
| PHASE B | | |
| 5 | Aqua (water) | 42.00 |
| 6 | Glycerin | 4.00 |
| 7 | Sodium chloride | 1.00 |
| 8 | Silica suspension containing 35% OMC | 25.00 |

Phase A and phase B were made separately. Phase B was added slowly to phase A with stirring (r.t.). The mixture was homogenized for 1 min.

Example 8
Comparative Example of Water in Oil Sunscreen Composition Containing Free OMC

|   | INCI name | % w/w |
|---|---|---|
| PHASE A | | |
| 1 | cetyl dimethicone copolyol | 3.00 |
| 2 | Isohexadecane | 9.50 |
| 3 | Cetearyl isonanoate | 7.75 |
| 4 | Octyl stearate | 7.75 |
| 5 | OMC | 8.80 |
| PHASE B | | |
| 6 | Aqua (water) | 58.20 |
| 7 | Glycerin | 4.00 |
| 8 | Sodium chloride | 1.00 |

Make phase A and phase B separately, at r.t. Add slowly phase B to phase A while stirring (r.t.). Homogenize for 1 min.

Example 9
Photostability Tests of Encapsulated Sunscreens Versus Free Sunscreen Active Ingredients One important example of preventing deleterious cross reactivity is the case OMC and BMDBM. It is widely recognized that when OMC and BMDBM are co-formulated, both of them show instability under illumination. This is a significant drawback, since each one of these sunscreen ingredients has high specific absorption at its peak. BMDBM is the only efficient UVA absorber currently used, while OMC is the most widely used UVB absorber.

Three formulations were made according to example 2, based on sunscreen active ingredients which are encapsulated in sol-gel silica, as described in example 1 with the compositions given in table 1. Sunscreen active ingredients were added as composite encapsulated sunscreen in aqueous suspension to the water phase. For comparison, three other formulations with same compositions were prepared with free sunscreen active ingredients, according to example 3.

The six samples were subjected to photostability test based on the method described by Diffey and Robson (B. L. Diffey and J. Robson, J. Soc. Cosmet. Chem. 40, 127–139, 1989). Sunscreen samples were applied to Transpore® tape, and illuminated with simulated solar light. The transmission through the combination was recorded with a Bentham double grating spectroradiometer. By repeating the measurement at increasing times, it is possible to estimate the stability of the film of sunscreen. Changes in transmission in a given wavelength range indicate that the chemical which absorbs in that wavelength range is not stable. The total intensity of the light in the range 290–400 nm was about 30 mW/cm$^2$, which compares with a figure of between 5 to 6 normal sunlight.

FIGS. 1–6 show the results obtained for the six samples. Comparison of the six figures shows clearly that the separate encapsulation of OMC and BMDBM prevents cross reactivity and enhance the photostability of the sunscreen composition most significantly. The instability of a composition containing OMC and BMDBM (in their free form) in the same formulation is demonstrated in FIG. 2. The change visualized in the transmittance spectra from line 2 to 4 over 20 minutes of illumination indicates rapid degradation of the absorbing compound, i.e. the sunscreen actives.

Figure 3:
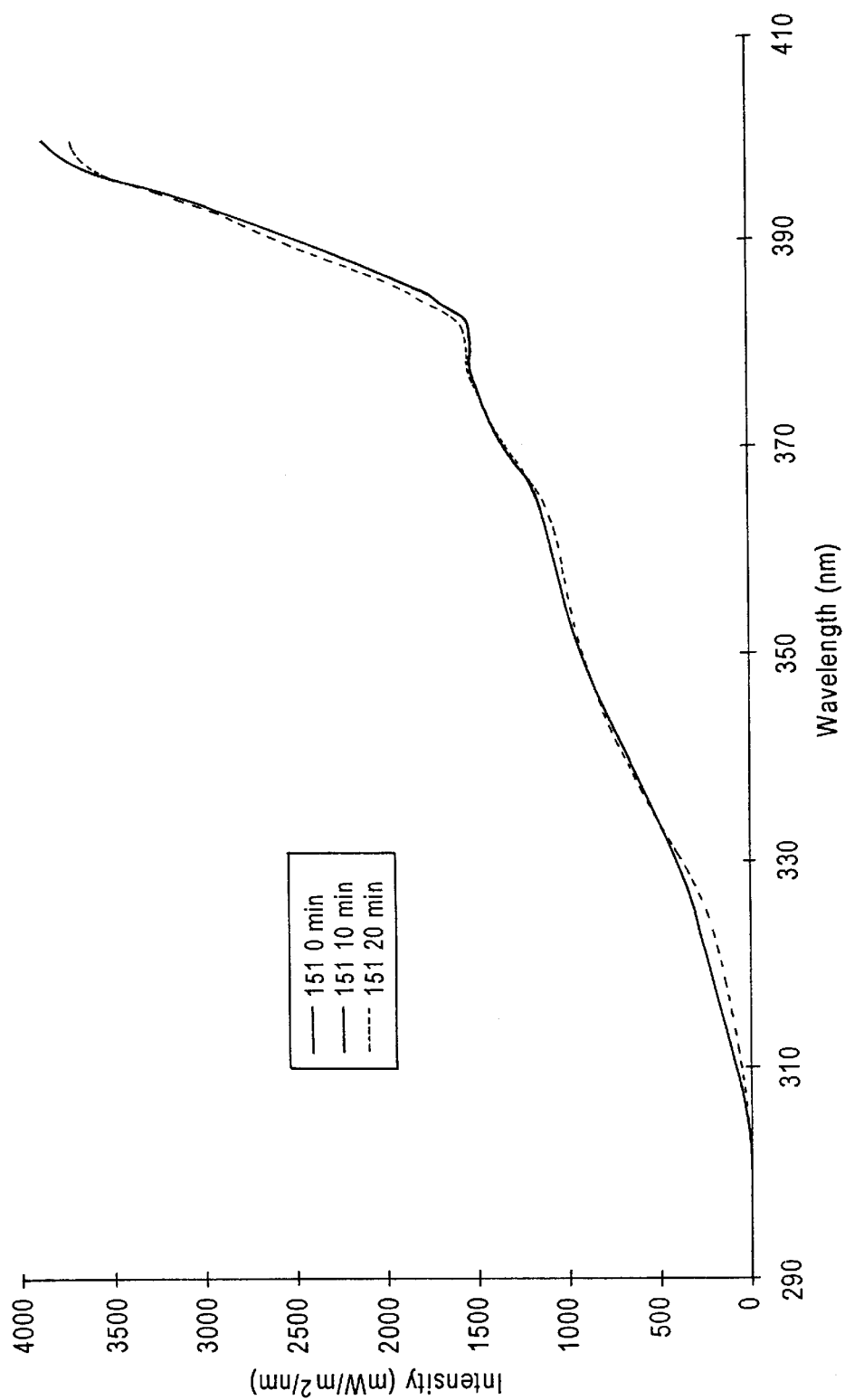
FIG. 3: transmittance spectra of sample 151 (containing encapsulated OMC and separately encapsulated BMDBM with HMS) during illumination: sample 151 at 0 min (line 1), 10 min (line 2) and 20 min illumination (line 3).
Figure 4:
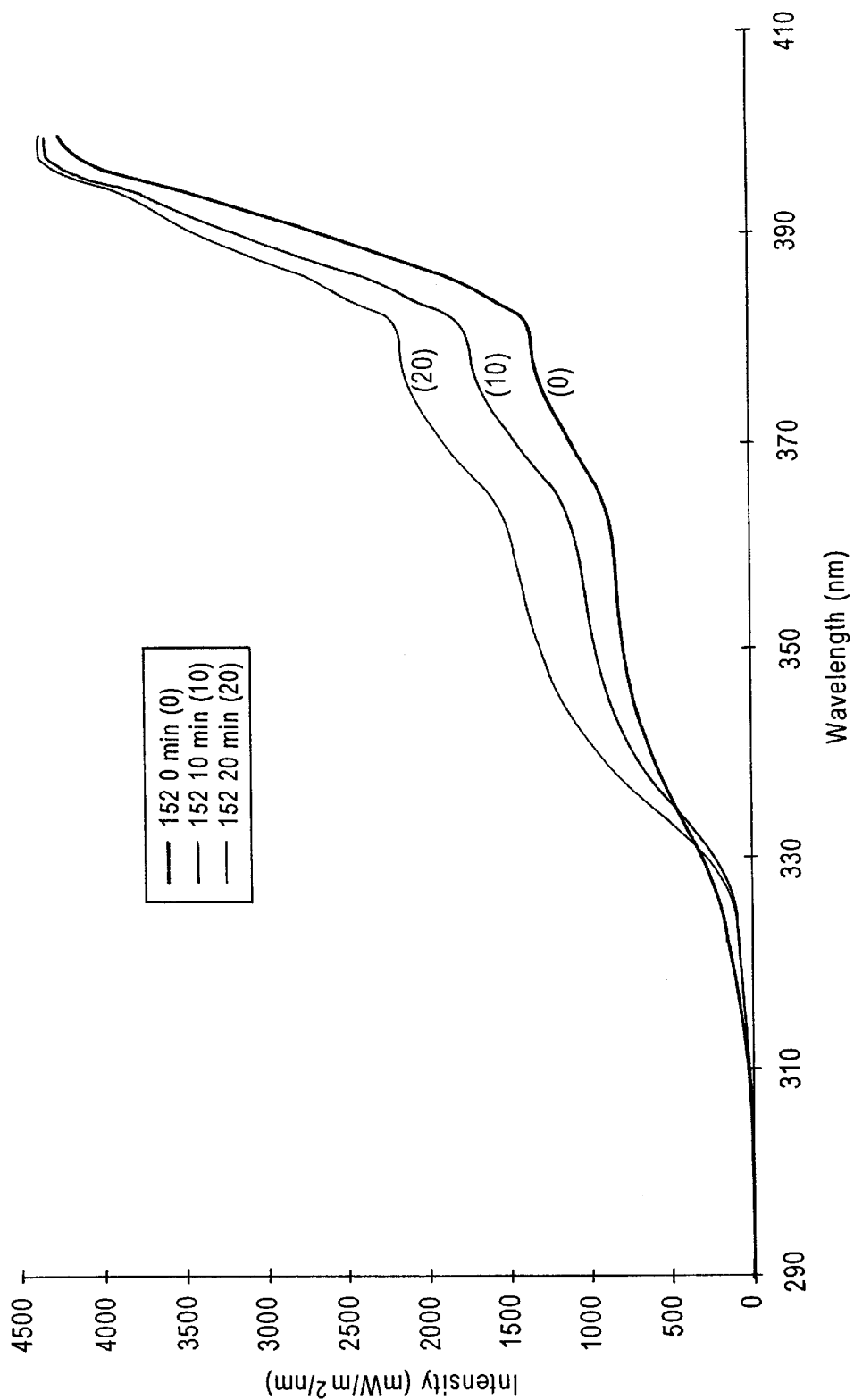
FIG. 4: transmittance spectra of sample 152 (containing free OMC, BMDBM and HMS) during illumination: sample 152 at 0 min (line 1), 10 min (line 2) and 20 min illumination (line 3).
Figure 5:
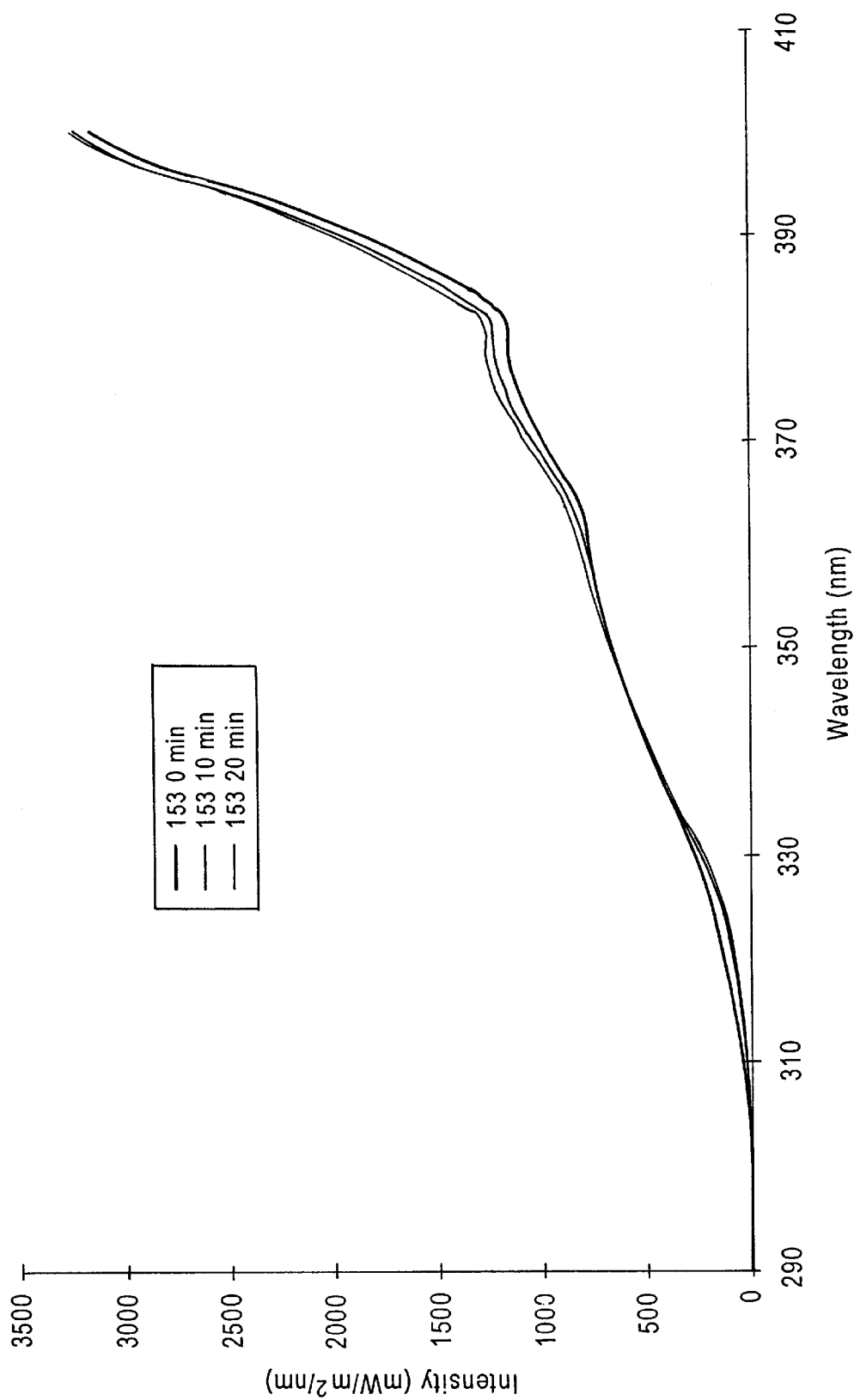
FIG. 5: transmittance spectra of sample 153 (containing encapsulated OMC and separately encapsulated BMDBM with Octocrylene) during illumination: sample 153 at 0 min (line 1), 10 min (line 2) and 20 min illumination (line 3).

In contrast, FIG. 3 shows the results obtained when OMC is separated from BMDBM by encapsulating OMC in one part, while encapsulating in other capsules a mixture of BMDBM and HMS. Both types of capsules are combined in the sunscreen composition according to example 2. It is clear in FIG. 3 that no change occurred in the transmittance spectrum over 20 minute illumination, indicating that the system is stable. In comparison, when the same sunscreen actives (OMC, BMDBM and HMS) are formulated in a similar sunscreen composition in their free form, illumination over 20 minutes results in decreasing transmittance, indicating degradation of the light absorbing compounds, i.e. the sunscreen actives.

Figure 6:
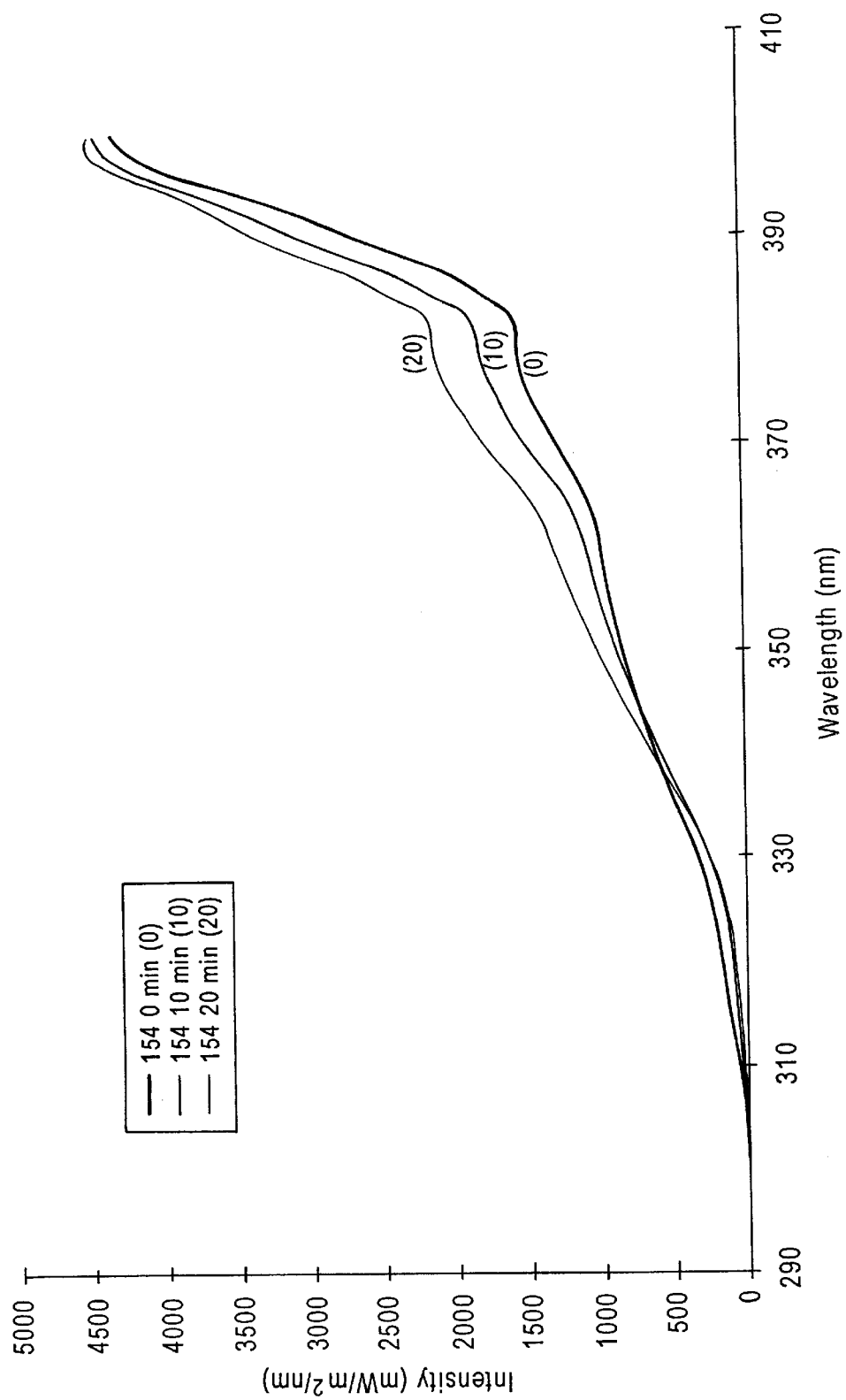
FIG. 6: transmittance spectra of sample 154 (containing free OMC, BMDBM and Octocrylene) during illumination: sample 154 at 0 min (line 1), 10 min (line 2) and 20 min illumination (line 3).

Similarly, when OMC is separated by encapsulation from a mixture of BMDBM and Octocrylene a photostable system is obtained (FIG. 5), whereas a composition containing the same active ingredients in their free form is less stable (FIG. 6).

As expected, co-encapsulation of OMC and BMDBM in the same capsule does not stabilize them, as seen in FIG. 1 (compare line 5, 6 and 7).

The results are summarized in Table 1.

TABLE 1

Photostability test results.

| Sample No. | Content | UVA stability | FIG. No. |
|---|---|---|---|
| 132(I) | Encapsulated (OMC + BMDBM)[a] | Unstable | 1 |
| 139 | Free (OMC + BMDBM)[a] | Unstable | 2 |
| 151(II) | Encapsulated OMC And Encapsulated (HMS + BMDBM)[b] | Stable | 3 |
| 152 | Free OMC, HMS, BMDBM[b] | Unstable | 4 |
| 153(I) | Encapsulated OMC And Encapsulated (octocrylene + BMDBM)[c] | Stable | 5 |
| 154 | Free OMC, octocrylene, BMDBM[c] | Moderately unstable | 6 |

[a]7.5% OMC, 1.4 BMDBM.
[b]OMC, 1.5 BMDBM, 5.4% HMS.
[c]7.5% OMC 1.5% BMDBM, 5.6% octocrylene.

Example 10
Photostability Tests of Encapsulated Sunscreens Versus Free Sunscreen Active Ingredients Cosmetic compositions were prepared according to example 2 to contain 7.5% OMC encapsulated in sol-gel silica and 1.5% BMDBM with 5% 2-cyano-3,3-diphenylacrylic acid 2-ethylhexyl ester (Octocrylene), co-encapsulated in separate sol-gel silica capsules. A comparative composition containing the same actives in free form was prepared according to example 3.

The compositions are applied on a YSI model 5793 standard Teflon membrane as the substrate. Spectral transmittance measurements are taken at 1 MED intervals of the thin film of the product, which is irradiated in situ with 0 to 10 MEDs continuous exposure to the calibrated solar light source.

The MED of the photostability solar simulator was calculated using the CIE Human Erythemal Action spectrum and was based on MED of 20 mJ, typical of a fair skinned individual.

Figure 7A:
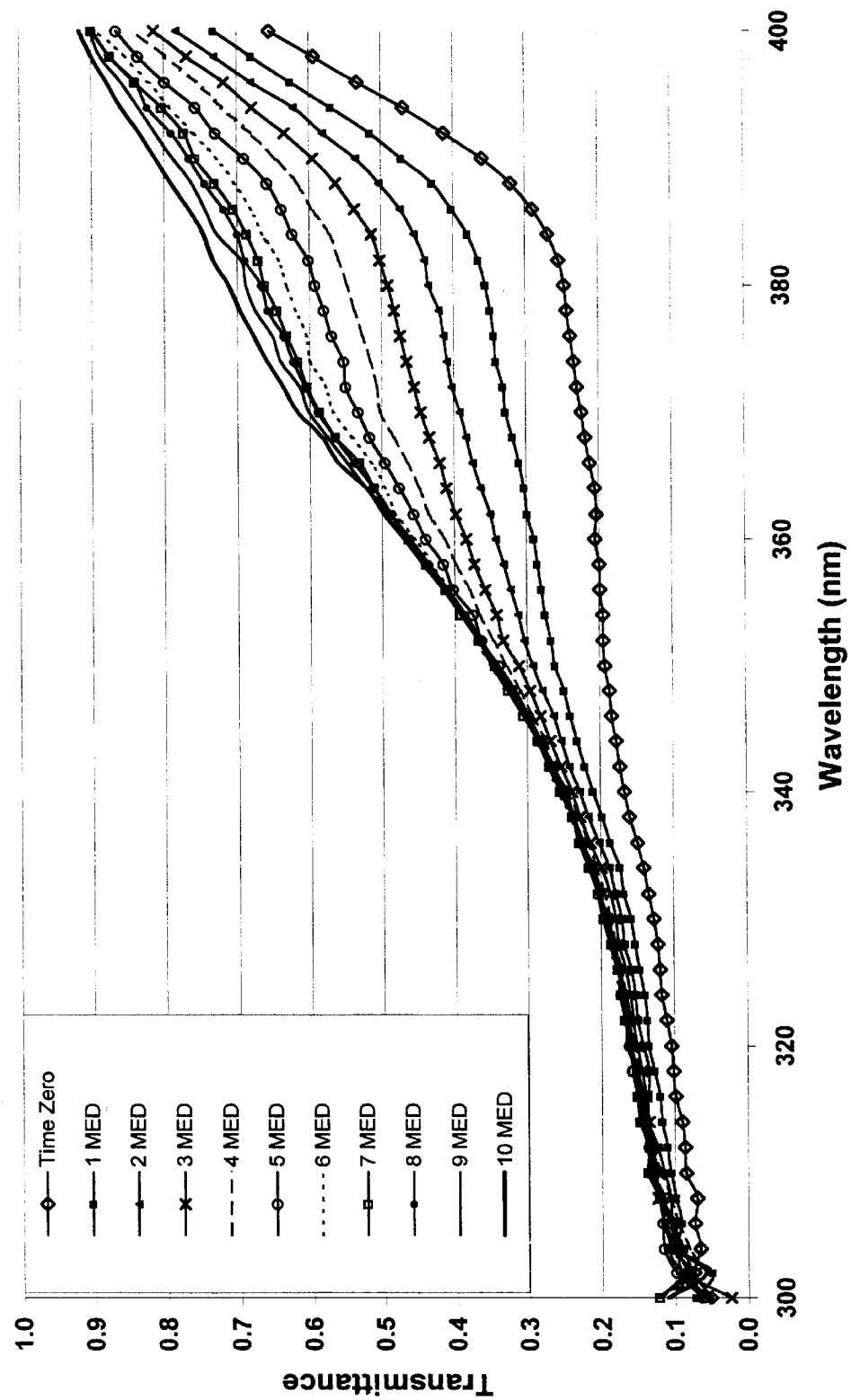
FIG. 7.A- transmittance spectra of a composition containing free sunscreen actives (7.5% OMC, 1.5% BMDBM and 5% Octorcrylene) at increasing MED [Minimal Erythemal Dose] doses.
Figure 7B:
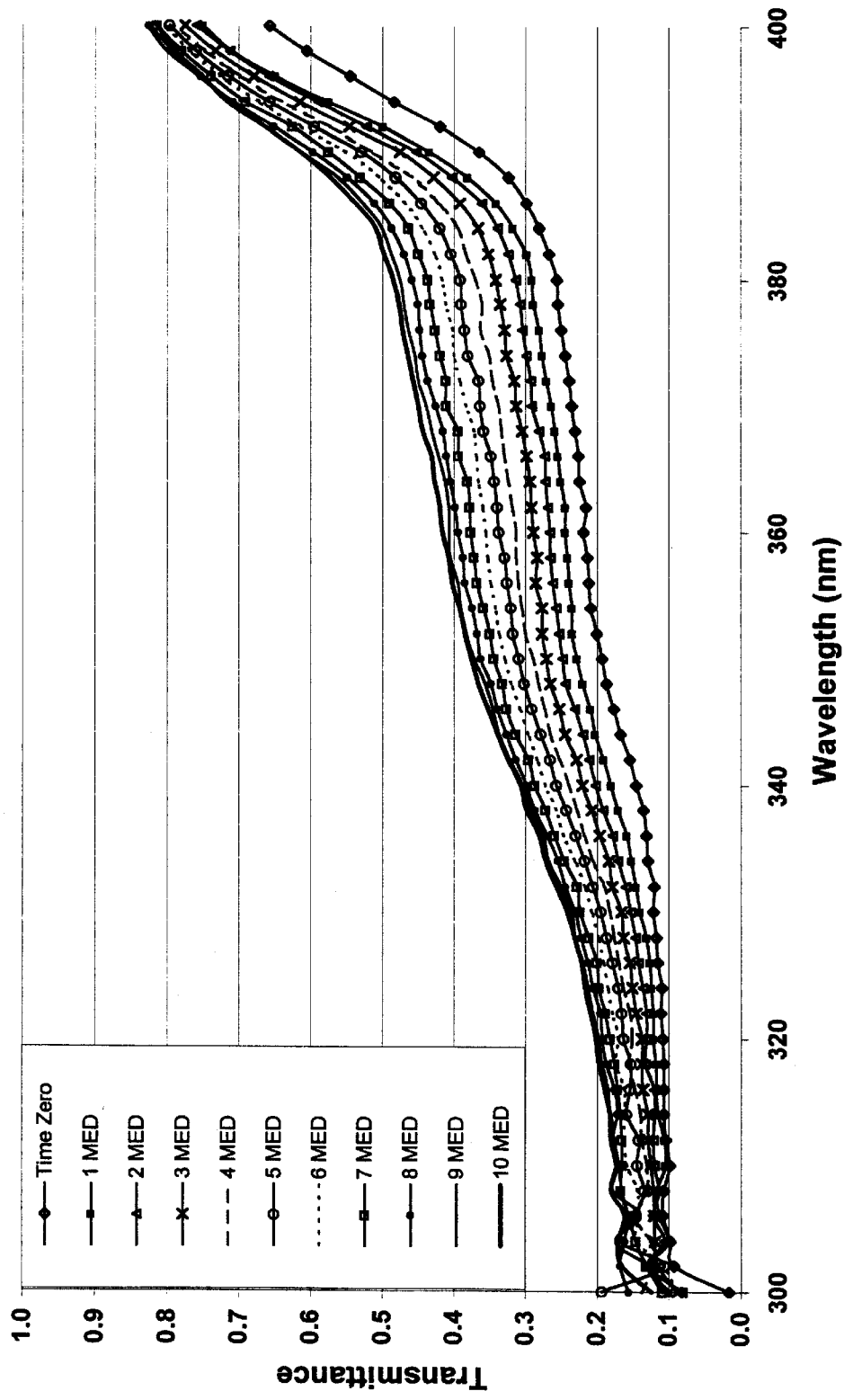

FIG. 7A shows the transmittance spectra of a composition containing free sunscreen actives, while FIG. 7B shows the spectra of a composition containing encapsulated OMC and encapsulated (BMDBM+Octocrylene). The best screening effect is obtained for both samples at 0 MED, as expected. The composition containing the free ingredients show rapid degradation of the actives, as seen from the increased transmittance at higher MEDs (FIG. 7A). It is observed that the stabilization effect of Octocrylene on BMDBM is not sufficient in the presence of OMC to prevent severe degradation of the sunscreen actives. Significantly slower degradation is observed when OMC is encapsulated separately from (BMDBM+Octocrylene), as seen in FIG. 7B.

What is claimed is:

1. A method of preparing a sunscreen composition with improved photostability that contains at least two sunscreen active ingredients, which are photo-unstable when formulated together, said method comprising the steps of:
   (a) separating said at least two sunscreen active ingredients from each other in the sunscreen composition by microencapsulating at least one of said active ingredients in sol-gel microcapsules made of an encapsulating material suitable for holding said encapsulated active ingredient; and
   (b) adding other components and additives needed for the preparation of said sunscreen composition.

2. A method according to claim 1 wherein said sunscreen active ingredients are selected from the group consisting of UVA absorbers and UVB absorbers.

3. A method according to claim 1 wherein said sunscreen composition contains at least one UVA absorber and at least one UVB absorber.

4. A method according to claim 1, wherein each of said active ingredients is encapsulated in separate said sol-gel microcapsules.

5. A method according to claim 1, wherein at least one of said sunscreen active ingredients, other than said encapsulated active ingredient, is not encapsulated.

6. A method according to claim 1 wherein one of the sunscreen active ingredients is a dibenzoylmethane derivative, selected from a group consisting of 4-tert-butyl-4'-methoxydibenzoylmethane, 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane and 2,6-dimethyl-4-tert-butyl-4'-methoxy-dibenzoylmethane.

7. A method according to claim 1 wherein the sunscreen active ingredients are 4-tert-butyl-4'-methoxydibenzoylmethane and 2-ethylhexyl 4-methoxycinnamate.

8. A method according to claim 6, wherein 4-tert-butyl-4'-methoxydibenzoylmethane is said encapsulated active ingredient, and is co-encapsulated in said micro capsules with homosalate or with 2-cyano-3,3-diphenylacrylic acid 2-ethylhexyl ester.

9. A method according to claim 6 wherein 4-tert-butyl-4'-methoxydibenzoylmethane is said encapsulated active ingredient, and is co-encapsulated in said micro capsules with a suitable cosmetic oil.

10. A method according to claim 9 wherein said cosmetic oil is selected from the group consisting of dicaprylyl maleate, Capric triglyceride, caprylic triglyceride, octyl palmitate, C12–C15 alkyl benzoate, dioctyl maleate, dioctyl malate, propylene glycol dicaprylate, propylene glycol dicaprate, diisopropyl adipate, hexyl laurate, and mixtures thereof.

11. A method according to claim 1 wherein the sunscreen active ingredients are 2-ethylhexyl p-methoxycinnamate and cinoxate.

12. A method according to claim 1 wherein at least one of said active ingredients is a physical sunblock active ingredient selected from the group consisting of titanium dioxide, zinc oxide, iron oxide, and mixtures thereof.

13. A method according to claim 12 wherein said physical sunblock ingredient is of any commercially available grade, including surface treated particles.

14. A method according to claim 13 wherein said surface treated particles are titanium dioxide particles which have been surface treated with silica, alumina, stearic acid or by any other surface treatment.

15. A method according to claim 1 wherein said sunscreen composition is incorporated into a cosmetically acceptable formulation for use for the protection of human epidermis or hair against UV radiation.

16. A method according to claim 1 wherein said sunscreen compositions is in the form of a lotion, a cream, a milk, a gel, an oil, an aerosol, a spray, a foam, a solid stick, a powder, a shampoo, a hair conditioner, a lacquer or a make up.

17. A method of preparing a sunscreen composition with improved photostability that contains at least two organic sunscreen active ingredients, which are photo-unstable when formulated together, said method comprising the steps of:
   (a) separating said at least two organic sunscreen active ingredients from each other in the sunscreen composition by microencapsulating at least one of said active ingredients in microcapsules made of an encapsulating material suitable for holding said at least one encapsulated active ingredient; and
   (b) adding other components and additives needed for the preparation of said sunscreen composition
   wherein at least one of said sunscreen active ingredients, other than said encapsulated active ingredient, is not encapsulated.

18. The method of claim 17, wherein said encapsulating material forms a diffusion barrier which prevents said encapsulated active ingredient from leaching outside of said microcapsules.

19. The method of claim 18, wherein said diffusion barrier further prevents said unencapsulated active ingredient from entering said microcapsules.

20. The method of claim 17, wherein said encapsulated active ingredient is microencapsulated in sol-gel microcapsules.

* * * * *